United States Patent [19]

Corman

[11] Patent Number: 5,105,812
[45] Date of Patent: Apr. 21, 1992

[54] NASOGASTRIC TUBE WITH REMOVABLE PH DETECTOR

[75] Inventor: John M. Corman, Houston, Tex.

[73] Assignee: Baylor College of Medicine, Houston, Tex.

[21] Appl. No.: 559,108

[22] Filed: Jul. 25, 1990

[51] Int. Cl.$^5$ .............................................. A61B 5/05
[52] U.S. Cl. .................................. 128/635; 128/780; 604/96; 604/165
[58] Field of Search ..................... 604/96-98, 604/100, 164, 165, 170, 264, 270; 606/192, 196; 128/632, 635, 636, 768, 771, 780, 772, 642

[56] References Cited

U.S. PATENT DOCUMENTS

| | | | |
|---|---|---|---|
| 3,373,735 | 3/1968 | Gallagher | 604/280 |
| 3,888,237 | 6/1975 | Mori | 128/635 |
| 4,381,011 | 4/1983 | Somers, III | 128/635 |
| 4,981,470 | 1/1991 | Bombeck, IV | 128/635 |

FOREIGN PATENT DOCUMENTS

| | | | |
|---|---|---|---|
| 3523987 | 1/1987 | Fed. Rep. of Germany | 128/635 |
| 9001894 | 3/1990 | PCT Int'l Appl. | 128/635 |
| 0178028 | 11/1966 | U.S.S.R. | 128/780 |
| 0735999 | 5/1980 | U.S.S.R. | 128/632 |
| 1102573 | 7/1984 | U.S.S.R. | 128/632 |

Primary Examiner—John D. Yasko
Assistant Examiner—Anthony Gutowski
Attorney, Agent, or Firm—Fulbright & Jaworski

[57] ABSTRACT

A method and apparatus for placing a nasogastric tube into a patient by inserting and releasably anchoring a pH detector in the bore of the tube adjacent the distal end. The detector is connected through the proximal end of the tube to a pH monitor. The tube and detector are inserted into the patient while monitoring the measured pH of the detector for determining the placement of the tube. After placing the tube, the detector is released from the bore of the tube and removed from the nasogastric tube while leaving the tube in the patient. The detector is releasably anchored by inflating a balloon connected to the detector.

7 Claims, 2 Drawing Sheets

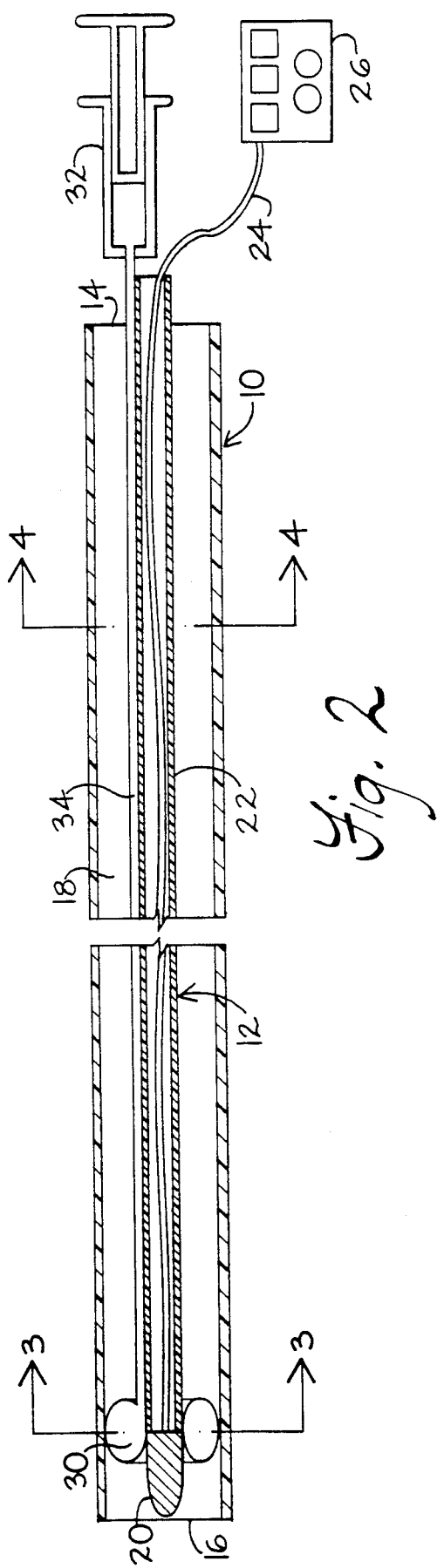

NASOGASTRIC TUBE WITH REMOVABLE PH DETECTOR

BACKGROUND OF THE INVENTION

A significant problem in the placement of nasogastric tubes is the accidental introduction of the tube into the trachea and the lungs rather than the esophagus. This problem is particularly apparent in intensive care settings where the patient is unable to assist in the placement of the nasogastric tube. Perforation of the lung by the nasogastric tube is a medical emergency. The pneumothorax or hemothorax that occurs requires the introduction of a chest tube in order to maintain ventilation of the patient. After the physician has introduced the nasogastric tube, an x-ray is always taken of the patient in order to insure that the tube is correctly placed. There is, of course, an inherent risk in x-rays.

It is known, as disclosed in U.S. Pat. Nos. 3,373,735 and 4,381,011, to provide a nasogastric tube with a pH detector for determining whether the distal end of the tube is entering the stomach rather than the lung because the pH of the stomach is uniquely acidic.

However, these prior art devices are integral with the nasogastric tube and therefore are not compatible with other types of nasogastric tubes and present the added risk of having the detector remain permanently in the stomach with the nasogastric tube thereby creating potential complications.

The present invention is directed to a method and apparatus for placing a flexible nasogastric tube into a Patient which is adapted to be used with any conventional nasogastric tube or enteral feeding device, which may be reusable or disposable, and which can be removed from the nasogastric tube after proper placement is confirmed thereby reducing the problem associated with leaving a detector in the patient for extended periods of time.

SUMMARY

The present invention is directed to an apparatus for placing a flexible nasogastric tube having a proximal end, a distal end, and a bore therein, into a patient. The apparatus includes a pH detector adapted to be removably inserted into the bore through the proximal end and positioned adjacent the distal end. Expandable and contractible anchor means are connected to the detector for releasably anchoring the detector in the bore adjacent the distal end of the tube, and control means are connected to the anchor and extendible out of the proximal end for controlling the expansion and contraction of the anchor means. Measuring means are connected to the pH detector and extendible out of the proximal end for monitoring the pH of the detector as the detector and nasogastric tube are inserted into a patient for determining the location of the distal end of the tube relative to the patient.

A further object of the present invention is wherein the anchor means may be an air inflatable balloon.

Still a further object of the present invention is wherein a second tube is provided having an outside diameter less than the bore and which is connected to the detector and the anchoring means to aid in the insertion and removal from the nasogastric tube. Preferably, the anchor means surrounds the second tube.

Yet a still further object of the present invention is the provision of a method of placing a nasogastric tube having a proximal end, a distal end, and a bore into a patient which includes inserting a pH detector into the bore of the tube and adjacent the distal end. The method includes releasably anchoring the detector in the bore adjacent the distal end and connecting the detector through the proximal end to a pH monitor. The method also includes inserting the tube and detector into the patient while monitoring the measured pH of the detector. After placement of the tube in the patient, the detector is released from the bore and removed from the nasogastric tube while leaving the tube in the patient.

A further object is wherein the detector is releasably anchored from outside the tube by inflating a balloon connected to the detector, and preferably the detector is inserted into and removed from the tube by the use of a second tube connected to the detector.

Other and further objects, features and advantages will be apparent from the following description of a presently preferred embodiment of the invention, given for the purpose of disclosure, and taken in conjunction with the accompanying drawing.

BRIEF DESCRIPTION OF THE DRAWING

FIG. 2 is an elevational view, partly in cross section, illustrating the placement of the pH detector of the present invention in position and anchored to the interior of a nasogastric tube, FIG. 3 is a cross-sectional view taken along the line 3—3 of FIG. 2, and FIG. 4 is a cross-sectional view taken along the line 4—4 of FIG. 2.

DESCRIPTION OF THE PREFERRED EMBODIMENT

Figure 1A:
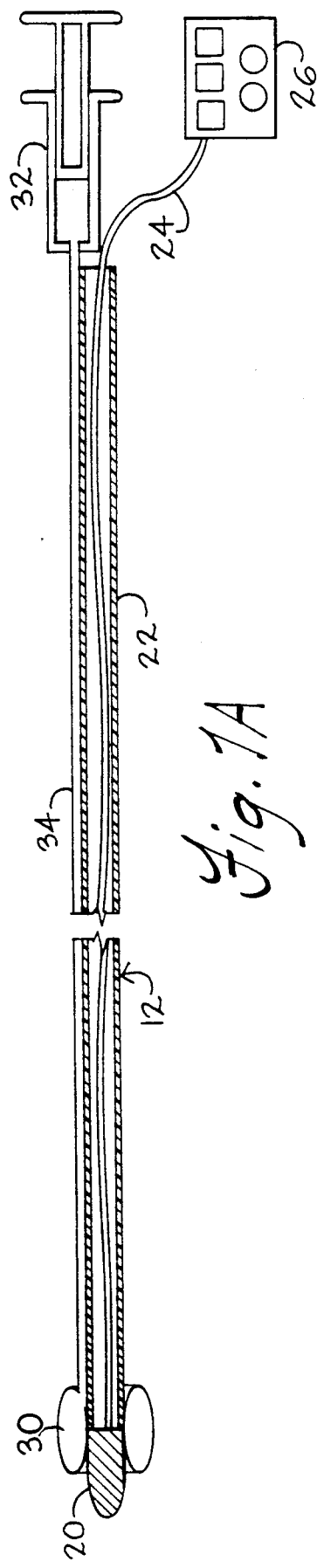
FIG. 1A is an elevation of view, partly in cross section, of a pH detector adapted to be removably inserted in the bore of the nasogastric tube of FIG. 1.
Figure 1:
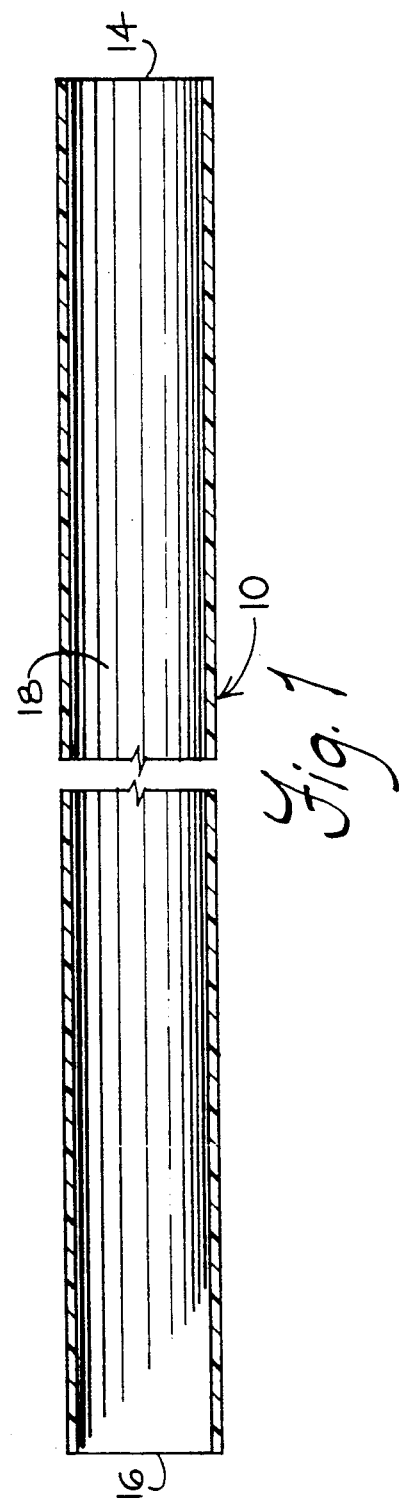
FIG. 1 is an elevational view, partly in cross section, of a nasogastric tube used in the present invention.

Referring now to the drawings, the reference numeral 10 generally indicates any suitable nasogastric tube for insertion into the esophagus and stomach and a pH detector generally indicated by the reference numeral 12 which is adapted to be releasably insertable into the tube 10.

The nasogastric tube 10 includes a proximal end 14, a distal end 16, and a bore 18 therein. The tube 10 may be any conventional nasogastric tube which is flexible and made out of any suitable material such as plastic. One satisfactory material is silicon. The present invention has the advantage that it may be used and is adaptable for use with any current nasogastric tube and thus does not require a special tube nor is it limited to specific embodiments as does prior art devices.

The pH detector 12 includes a pH electrode 20 for measuring the pH of the environment in which the electrode 20 is placed. Preferably, the electrode 20 is supported from a second tubular member 22 for insertion of and removal of the electrode 20 from the bore 18 of the nasogastric tube 10. Suitable signal lines 24 are connected to the electrode 20 and extend through the interior of the second tube 22 to a pH meter 26. Thus, the pH detector 12 is adapted to be inserted into and removed from the bore 18 of the nasogastric tube 10 through the proximal end 14 and positioned adjacent the distal end 16 as best seen in FIG. 2.

In order to maintain the position of the electrode 20 adjacent the distal end 16 of the tube 10 as it is being inserted into a patient, an expandable and contractible anchor means 30 is provided connected to the detector 12 for releasably anchoring the detector 12 in the bore 18 of the tube 10 adjacent the distal end 16 as best seen in FIG. 2. Preferably, the anchor means is a resilient air inflatable balloon which surrounds the detector 12. The balloon 30 may be inflated by any conventional means, here shown as a syringe 32 connected to an air line 34 to the balloon 30 for inflating or releasing air from the balloon 30.

The electrode 20 may be any conventional electrode capable of detecting the pH of body fluids and the pH meter 26 may be any conventional meter. A suitable combined pH electrode and meter is Model No. 93-2000 sold by Cnetics Medical Incorporated.

In use, the pH detector 12 is inserted into the bore 18 of the nasogastric tube 14 through the proximal end 14 and positioned with the electrode 20 adjacent the distal end 16 of the tube 10. The anchor or balloon 30 is inflated to hold the pH electrode 20 adjacent the distal end 16. And the electrode 20 is connected through the lines 24 to the pH monitor 26. Thereafter, the nasogastric tube 10 along with the attached pH detector 12 is fed into the esophagus with the distal end 16 being fed first into the patient's body. As the distal end 16 is being fed into the patient, the pH of the body fluids being encountered is monitored by the meter 26. By monitoring the pH of the detector 20, the placement of the distal end 16 of the tube 10 can be determined. That is, the operator can be sure that the distal end 16 enters the stomach rather than the lung because the pH of the stomach is uniquely acidic. The operator will know that the tube 10 has incorrectly entered the lung if the pH has not dropped appropriately. Therefore, an x-ray is not required for determining the position of the tube 10.

Once the physician is satisfied that the nasogastric tube is properly placed in the patient's body, the anchor or balloon 30 is released from the bore 18 by deflating the balloon 30 and the detector 12 including the second tube 22, the electrode 20, and the balloon 30 is removed for sterilization and reuse if desired. It is to be noted that the nasogastric tube 10 is left in place in the patient and therefore avoids the problem of the prior art of leaving a pH detector in the patient for extended periods of time.

Therefore, the present invention is advantageous in that the detector 12 is adaptable to any conventional or currently available nasogastric tube or enteral feeding device, it may be reusable or disposable, and it can be removed after proper placement of the nasogastric tube is confirmed thereby avoiding the inherent problems of leaving anything in the patient that is not necessary.

The present invention, therefore, is well adapted to carry out the objects and attain the ends and advantages mentioned as well as others inherent therein. While a presently preferred embodiment of the invention has been given for the purpose of disclosure, numerous changes in the details of construction, arrangement of parts, and steps of the process, will be readily apparent to those skilled in the art, and which are encompassed within the spirit of the invention and the scope of the appended claims.

What is claimed is:

1. An apparatus for placing a flexible nasogastric tube into a patient comprising, a flexible nasogastric tube having a proximal end, a distal end, and a bore, a pH detector positioned in the bore and positioned adjacent the distal end and adapted to be removed from the proximal end, expandable and contractible anchor means connected to the detector releasably anchoring the detector in the bore adjacent the distal end of the tube, control means connected to the anchor and extendable out of the proximal end for controlling the expansion and contraction of the anchor means, and measuring means connected to the pH detector and extendable out of the proximal end for monitoring the pH of the detector.

2. The apparatus of claim 1 wherein the anchor means is an air inflatable balloon.

3. The apparatus of claim 1 including a second tube having an outside diameter less than the bore and connected to the detector and the anchor means.

4. The apparatus of claim 3 wherein the anchor means surrounds the second tube.

5. The method of placing a nasogastric tube having a proximal end, a distal end, and a bore into a patient comprising, inserting a pH detector into the bore of the tube and adjacent the distal end, releasably anchoring the detector in the bore adjacent the distal end, connecting the detector through the proximal end to a pH monitor, inserting the tube and anchored detector into the patient while monitoring the measured pH of the detector, after placing the tube in position in the body, releasing the detector from the bore, and removing the detector from the nasogastric tube while leaving the tube in the patient.

6. The method of claim 5 wherein the detector is releasably anchored from outside the tube by inflating a balloon connected to the detector.

7. The method of claim 5 wherein the detector is inserted into and removed from the tube by the use of a second tube connected to the detector.

* * * * *